United States Patent
Wang et al.

(10) Patent No.: US 10,016,413 B2
(45) Date of Patent: Jul. 10, 2018

(54) COMBINATION DOPAMINE ANTAGONIST AND OPIATE RECEPTOR ANTAGONIST TREATMENT OF ADDICTIVE BEHAVIOR

(71) Applicants: Jia Bei Wang, Ellicott City, MD (US); Sarah Sushchyk, Baltimore, MD (US)

(72) Inventors: Jia Bei Wang, Ellicott City, MD (US); Sarah Sushchyk, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 96 days.

(21) Appl. No.: 14/025,434

(22) Filed: Sep. 12, 2013

(65) Prior Publication Data

US 2014/0073664 A1    Mar. 13, 2014

Related U.S. Application Data

(60) Provisional application No. 61/700,591, filed on Sep. 13, 2012.

(51) Int. Cl.
| | | |
|---|---|---|
| *A01N 43/40* | (2006.01) | |
| *A61K 31/473* | (2006.01) | |
| *A61K 31/485* | (2006.01) | |
| *A61K 45/06* | (2006.01) | |
| *A61K 31/4745* | (2006.01) | |

(52) U.S. Cl.
CPC .......... *A61K 31/485* (2013.01); *A61K 31/473* (2013.01); *A61K 31/4745* (2013.01); *A61K 45/06* (2013.01)

(58) Field of Classification Search
CPC .................................................. A61K 31/198
USPC ....................................................... 514/350
See application file for complete search history.

(56) References Cited

U.S. PATENT DOCUMENTS

2011/0092805 A1*   4/2011   Estevez .................. A61B 5/055
                                                            600/419

OTHER PUBLICATIONS

Cheong et al. (Modulation of Corydalis tuber on Glycine-Induced Ion Current in Acutely Dissociated Rat Periaqueductal Gray Neurons. Biol. Pharm. Bull. 27(8) 1207-1211 (2004)).*
Mantsch et al. (Levo-tetrahydropalmatine attenuates cocaine self-administration and cocaine-induced reinstatement in rats). Psychopharmacology (Berl). Jul. 2007;192(4):581-91. Epub Mar. 15, 2007).*
Glennon et al. (Drug Discrimination: Applications to Medicinal Chemistry and Drug Studies, p. 308-309, May 9, 2011).*
Jin et al. (Tetrahydroprotoberberine—a new chemical type of antagonist of dopamine receptors. Sci Sin B. May 1986;29(5):527-34).*
Sell et al. (Cocaine and amphetamine attenuate the discriminative stimulus effects of naltrexone in opioid-dependent rhesus monkeys. J Pharmacol Exp Ther. Jun. 2002;301(3):1103-10).*
Mantsch et al. (Levo-Tetrahydropalmatine Attenuates Cocaine Self-Administration under a Progressive-Ratio Schedule and Cocaine Self-Administration under a Progressive-Ratio Schedule and Cocaine Discrimination in Rats. Biomedical Sciences Faculty Research and Publications. Dec. 1, 2010).*

* cited by examiner

*Primary Examiner* — Layla Soroush
(74) *Attorney, Agent, or Firm* — Benjamin Aaron Adler

(57) ABSTRACT

The present invention is directed to a method of treating or preventing an addictive behavior in a subject, said method comprising administering to said subject an effective amount of a dopamine antagonist and a opiate receptor antagonist or a composition comprising same. Further provided are pharmaceutical compositions comprising, as active substances, at least one dopamine antagonist and at least one opiate receptor antagonist.

2 Claims, 3 Drawing Sheets

COMBINATION DOPAMINE ANTAGONIST AND OPIATE RECEPTOR ANTAGONIST TREATMENT OF ADDICTIVE BEHAVIOR

STATEMENT OF FEDERALLY SPONSORED RESEARCH

This invention was made with government support under Grant No. DA031401 awarded by the National Institutes of Health. The government has certain rights in the invention.

CROSS-REFERENCE TO RELATED APPLICATION

This application is a non-provisional under 35 U.S.C. 119(e) of provisional application U.S. Ser. No. 61/700,591, filed Sep. 13, 2012, now abandoned, the entirety of which is hereby incorporated by reference.

BACKGROUND OF THE INVENTION

Field of the Invention

The present invention relates generally to the use of combination therapies to addiction-related or neurological diseases and disorders, particularly substance-dependence diseases or disorders that include addiction to cocaine, opioids, nicotine, cannabis and other psychostimulants and potentially other mental or neurological illnesses.

Description of the Related Art

Cocaine, one of the oldest known drugs, is a powerfully addictive stimulant that directly affects the brain. The pure chemical, cocaine hydrochloride, has been an abused substance for more than 100 years, and coca leaves, the source of cocaine, have been ingested for thousands of years. Today, cocaine use ranges from occasional use to repeated or compulsive use, with a variety of patterns between these extremes. There is no safe way to use cocaine and any route of administration can lead to absorption of toxic amounts of cocaine, leading to acute cardiovascular or cerebrovascular emergencies that could result in sudden death. Repeated cocaine use by any route of administration can produce dependence, addiction and other adverse health consequences.

Cannabis, i.e., marijuana and cannabinoids, is the most commonly used illicit drug in developed countries, and the lifetime prevalence of marijuana dependence is the highest of all illicit drugs in the United States. Human studies have demonstrated that a significant subset of chronic cannabis users have difficulty quitting cannabis use and consistently exhibit a cluster of withdrawal symptoms after abrupt cessation of cannabis use. Such symptoms include disturbances in sleep and affect, e.g., irritability, restlessness, anxiety, and dysphoria or depression. Many chronic cannabis users report an average of 6.4 withdrawal symptoms of at least moderate severity, a number that exceeds the criteria set by American Psychiatric Association for substance-withdrawal disorders. However, there are currently no accepted pharmacotherapies for the management of cannabis withdrawal. Existing treatments are all of limited efficacy and do not address undesirable consequences of early abstinence from cannabis, e.g., negative affect and sleep disturbance that may prompt relapse.

Despite decades of basic and clinical research there are currently no medications available to treat cocaine dependence, addiction, overdose or to help prevent relapse. Thus, therapies are needed which can treat such dependence-related disorders.

There is a need for better means for preventing relapse to alcohol dependence and for treating symptoms or disorders associated with protracted abstinence. There is also a need in the art for effective treatment for drug dependence and withdrawal. The present invention addresses these and other needs.

SUMMARY OF THE INVENTION

The present invention is directed to a method of treating or preventing an addictive behavior in a subject, said method comprising administering to said subject an effective amount of a dopamine antagonist and an opiate receptor antagonist or a composition comprising same. The addiction is a physical dependence to an addictive agent or to an addictive behavior. Representative examples of the addictive agent include but are not limited to cocaine, crack, morphine and morphine-like compounds, opioids, heroin, ecstasy, LSD, ketamine, tobacco, alcohol, or combinations thereof, caffeine, nicotine, cannabis and cannabis derivatives, phencyclidine and phencyclidine-like compounds, sedative hypnotics, pain-killers, psychostimulants, amphetamines and amphetamine-related drugs. Representative examples of the pain-killer include but are not limited to alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene sufentanil, tramadol and tilidine. Representative examples of the addictive behavior include but are not limited to obsessive compulsive disorder, compulsive spending and/or gambling, pathological overeating, pathological use of electronic devices and communication devices such as cellular phones, pathological use of electronic video games, addiction to pornography and sex, eating disorders such as anorexia and bulimia, kleptomania, pyromania, compulsive over-exercising and overworking. Representative examples of the dopamine antagonist include but are not limited to levo-tetrahydropalmatine, domperidone, the pharmaceutically acceptable salts of domperidone, metoclopramide, the pharmaceutically acceptable salts and solvates of metoclopramide, bromopride, the pharmaceutically acceptable salts of bromopride, clebopride, the pharmaceutically acceptable salts of clebopride, alizapride and the pharmaceutically acceptable salts of alizapride. Representative examples of the opiate receptor antagonist include but are not limited to naltrexone, naltrexone, naloxone, nalmefene, cyclazocine, diprenorphine, etazocine, levalorphan, metazocine, nalorphine, and salts thereof.

The present invention is further directed to a method of treating or preventing an addictive behavior in a subject, said method comprising administering to said subject an effective amount of a dopamine antagonist and an opiate receptor antagonist or a composition comprising same and further comprising administering at least one additional compound capable of preventing or treating an addiction to a drug or withdrawal from drug consumption. Representative examples of the additional compound include but are not limited to methadone, buprenorphine, naltrexone, acamprosate, disulfuram, topiramate, bupropion, rimonabant, disulfuram, modafinil, propranolol, baclofen, ondansetron, or combinations thereof.

The present invention is further directed to a pharmaceutical composition comprising, as active substances: at least one dopamine antagonist and at least one opiate receptor antagonist. Representative examples of the dopamine antagonist include but are not limited to levo-tetrahydropalmatine, domperidone, the pharmaceutically acceptable salts of domperidone, metoclopramide, the pharmaceutically acceptable salts and solvates of metoclopramide, bromopride, the pharmaceutically acceptable salts of bromopride, clebopride, the pharmaceutically acceptable salts of clebopride, alizapride and the pharmaceutically acceptable salts of alizapride. Representative examples of the opiate receptor antagonist include but are not limited to naltrexone, naltrexone, naloxone, nalmefene, cyclazocine, diprenorphine, etazocine, levalorphan, metazocine, nalorphine, and salts thereof. The composition is preferably formulated as levo-tetrahydropalmatine:naltrexone at a ratio of 10:1 to 50:1.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

DETAILED DESCRIPTION OF THE INVENTION

Definitions

Figure 1:
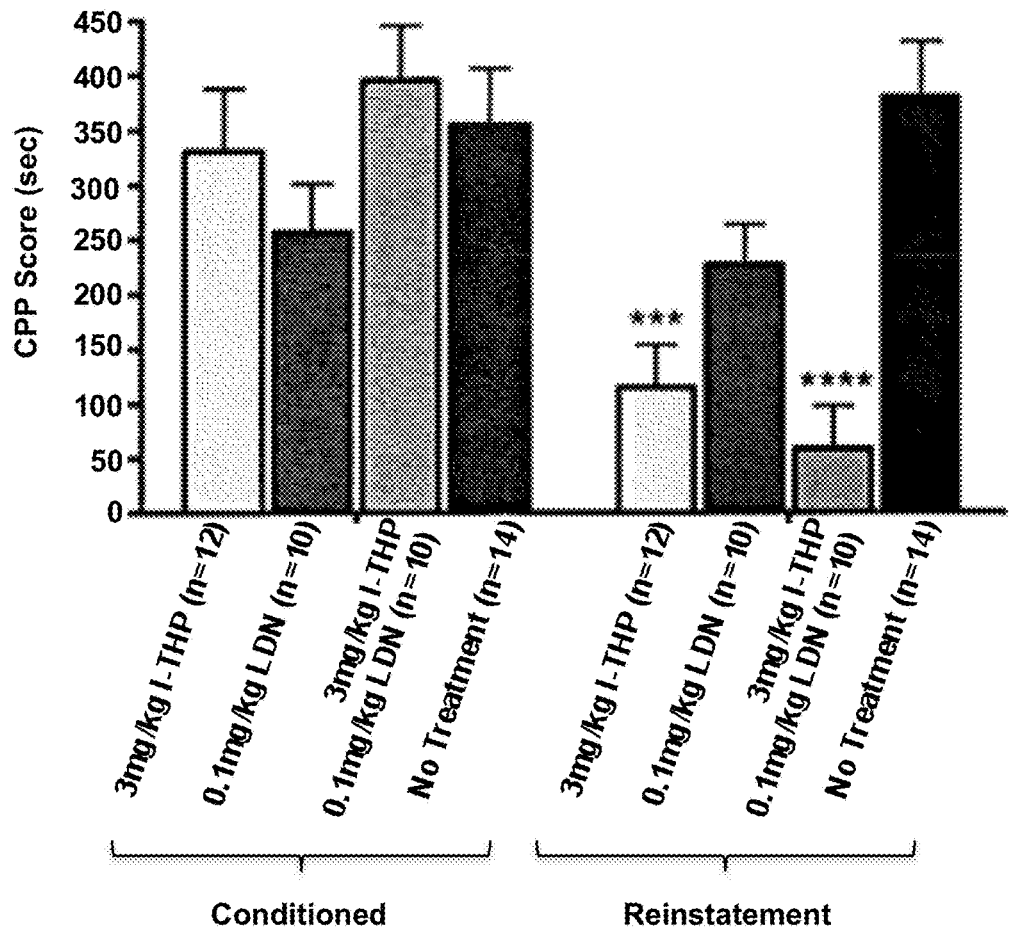
FIG. 1 shows the effects of treatment on cocaine induced reinstatement of CPP. Animals were conditioned using 10 mg/kg cocaine for 4 days, and reinstated using 5 mg/kg cocaine. Reinstatement was carried out 48 hours after CPP was extinct. The CPP score is calculated as a change in baseline from the cocaine conditioned chamber. A two way ANOVA followed by Bonferroni post test comparisons was used for analysis of the effect of treatment on cocaine reinstatement.

Unless otherwise noted, technical terms are used according to conventional usage. Definitions of common scientific technical terms may be found, for example, in Mcgraw-hill Dictionary of Scientific & Technical Terms published by Mcgraw-hill Healthcare Management Group; Benjamin Lewin, Genes VIII, published by Oxford University Press; Kendrew et al. (eds.), The Encyclopedia of Molecular Biology, published by Blackwell Publishers; and Robert A. Meyers (ed.), Molecular Biology and Biotechnology: a Comprehensive Desk Reference, published by Wiley, John & Sons, Inc; and other similar technical references.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As it is intended herein, an "addiction" to a drug is defined, in particular, by a drug consumption which is no longer controlled by the individual and which persists despite its possible negative consequences, which may be present or foreseeable, on the individual, in particular in an individual who is aware or who is informed of the possible negative consequences. The combination drug therapy of the present invention makes it possible to avoid or limit the establishment of an addiction and to reduce or eliminate an addiction that has already established. Thus, in particular, the combination drug therapy enables the individual in a situation of addiction to a drug to control, and in particular to stop, the consumption of the drug.

As used herein, the term "treatment" or any lingual variation thereof refers to obtaining beneficial or desired results, including and preferably clinical results. The treatment according to the invention involves optionally either the reducing or amelioration of any one symptom or condition which is indicative or characteristic of addiction or relapse, or delaying the progression of such a symptom or condition. In some embodiments, the treatment results in withdrawal from addiction.

As it is intended herein, the "withdrawal" from drug consumption in an individual is defined, in particular, by the stopping of the consumption of the drug in an individual, in particular in an individual in a situation of addiction with respect to the drug. According to the invention, the combination drug therapy of the present invention facilitates withdrawal and make it possible, in particular, to reduce the relapse i.e. renewed drug consumption again, risk or probability of an individual who has undergone withdrawal or who is abstinent, i.e. who has stopped consuming a drug, in particular a drug with respect to which he was in a situation of addiction.

In particular, the combination drug therapy of the present invention make it possible to prevent or treat the urge to consume a drug, in particular in an individual who has undergone withdrawal from a drug with respect to which he was in a situation of addiction or on which he was dependent. The urge, often described as intense, to consume a drug is also denoted as a craving.

Preferably, the individual according to the invention is a human being. The individual according to the invention exhibits in particular a drug addiction or a dependence, or is in a state of addiction, with respect to the drug according to the invention.

As it is intended herein, the drugs according to the invention encompass all the compounds liable of inducing a dependence or an addiction in an individual consuming them. The drugs according to the invention can in particular be referred to as "an addictive drug" or "a drug of abuse". The drug consumption according to the invention can be carried out by routes of any type, for example by ingestion, inhalation, or subcutaneous or intravenous injection. The drugs according to the invention can in particular be narcotics, medicaments, tobacco or alcohol. Preferably, the drugs according to the invention are selected from the group consisting of cocaine, crack, cannabis, morphine, opioids, heroin, ecstasy, LSD, amphetamines, ketamine, tobacco and alcohol. As will be clear to those skilled in the art, tobacco addiction according to the invention is generally a nicotine addiction and alcohol addiction according to the invention is generally an ethanol addiction.

As it is intended herein, the term "cannabis" groups together all or any of the psychoactive cannabinoids, including in particular tetrahydrocannabinol (THC). The term "opioid", for its part, denotes all or any of the psychoactive opioids or of the psychoactive derivatives of morphine.

Similarly, the term "prevention" or any lingual variation thereof refers to arresting or delaying the onset or recurrence of a symptom or condition associated with addiction, or preventing the occurrence or recurrence of such symptoms.

Particularly preferably, the drug of abuse according to the invention is nicotine, cocaine or crack, in particular nicotine or cocaine. The term "cocaine" groups together, or denotes without distinction, cocaine in itself and also its various salts, such as cocaine hydrochloride.

As demonstrated herein, the inventors of the invention disclosed in the present application have discovered that a combination drug therapy is efficient in treating a variety of additive behaviors and are additionally useful in suppressing relapse into addiction in subjects susceptible to regressing back to addictive state.

Thus, in an aspect of the invention there is provided a method of treating or preventing an addictive behavior in a subject, said method comprising administering to said subject an effective amount of a dopamine antagonist and an opiate receptor antagonist or a composition comprising same. The subject may be any animal, including a mammal, and particularly, a human.

In some embodiments, the addictive behavior is exhibited by said subject, following an unintentional or intentional exposure of said subject to at least one stimulus, trigger or cue, which induces in said subject an addictive behavior. In other words, the at least one stimulus may cause the subject to relapse into full or partial addiction to at least one agent or behavior. In some embodiments, said subject to be treated in accordance with the invention has been previously reduced or eliminated use of the addictive agent or practice of the addictive or compulsive behavior in response to treatment with an effective amount of an anti-addiction treatment, and/or wherein the subject is no longer exposed to an effective amount of the anti-addiction treatment. Thus, the invention also contemplates a method for preventing relapse into addiction. The method of the invention is also useful in reducing the addictive effect of re-exposure or continuous exposure to at least one agent, behavior or stimulus which induces the addictive behavior in an addicted subject or in a subject having a risk of developing an addiction. In some embodiments, the addiction is not induced by re-exposure or continuous exposure to at least one agent or behavior.

In another aspect, the invention provides a method of treating or preventing or reducing the probability of relapse to addiction, relapse use of an addictive agent or practice of an addictive or compulsive behavior in a subject, the method comprising administering to said subject an effective amount of a dopamine antagonist and a opiate receptor antagonist or a composition comprising same.

The treatment with said at least one dopamine antagonist and opiate receptor antagonist or a composition comprising same may be achieved by systemic administration, thereby said at least one dopamine antagonist and opiate receptor antagonist or a composition comprising same passes the blood-brain barrier, and may be administered parenterally, for example, via intravenous administration. In some other embodiments, the dopamine antagonist and opiate receptor antagonist or a composition comprising same is administered orally or by other routes known to one of ordinary skill in this art.

The dopamine antagonist and the opiate receptor antagonist or a composition are typically administered in an amount effective to achieve a desired result of changing addiction-related behavior of the subject. The "effective amount" for purposes herein is determined by such considerations as may be known in the art. The amount must be effective to achieve the desired effect on addiction, depending, inter alia, on the type and severity of the addiction to be treated and the treatment regime. The "effective amount" or "therapeutically effective amount" is the amount effective to achieve the specified result of changing addiction-related behavior by a subject, the sufficient to affect a desired biological or psychological effect. As generally known, an effective amount depends on a variety of factors including the affinity of the one dopamine antagonist or the opiate receptor antagonist, the distribution profile within the body, a variety of pharmacological parameters such as half life in the body, on undesired side effects, if any, on factors such as age and gender, etc. It should be emphasized, however, that the invention is not limited to any particular dose.

Generally speaking, addiction is defined as an uncontrolled and compulsive use (or abuse) of an agent or a behavioral pattern which is considered as an addictive behavior, even where the addictive behavior presents no harm to the subject practicing the behavior or to any other person associated with the subject. Within the scope of the present invention, the addictive behavior to be controlled, suppressed, minimized or diminished (by way of treatment or prevention) may be of two types: physiological and psychological. Addictions in general often express both physical and psychological features.

In some embodiments, the addiction to be treated or prevented as disclosed herein is a physical dependence to an agent (an addictive agent) or to a particular behavioral pattern. The addiction expressing a physical dependence may be to an agent generally selected from illicit drugs, prescription drugs (and OTC drugs), alcohol or any combination thereof, which agent is referred to herein as the "addictive agent". Generally speaking, the agent causes a recurring compulsion by an individual to engage in use and abuse of the agent, despite harmful consequences to the individual's health, mental state or social life. The term "addictive behavior" similarly refers to a behavioral compulsion, such as gambling, and compulsive overeating, as further detailed hereinbelow.

In some embodiments, the addiction is caused by an addictive agent, being optionally selected amongst addictive recreational drugs and addictive medications.

In some embodiments, the addictive agent is selected from alcohol, caffeine, nicotine, cannabis and cannabis derivatives, opiates and morphine-like compounds, phencyclidine and phencyclidine-like compounds, sedative hypnotics, psycho-stimulants, amphetamines and amphetamine-related drugs. In additional embodiments, the addictive agent is selected from alcohol, caffeine, nicotine, cannabis, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine and methylamphetamine. In other embodiments, the addictive agent is selected amongst pain-killer such as alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene sufentanil, tramadol, tilidine and any combination of any of the aforementioned agents. In yet additional embodiments, the addictive agent is selected from alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tilidine and tramadol. In some embodiments, the addiction is to cocaine.

In some embodiments, the addiction is in the form of a compulsive behavior (addictive behavior) and may be selected from obsessive compulsive disorder, compulsive spending and/or gambling, pathological overeating, pathological use of electronic devices and communication devices such as cellular phones, pathological use of electronic video games, addiction to pornography and sex, eating disorders such as anorexia and bulimia, kleptomania, pyromania, compulsive over-exercising and overworking.

In some embodiments, the addiction is to two or more addictive agents and/or addictive behavior. In some embodiments, one or both of the addictions are to an addictive agent.

The compositions employed by the methods of the invention may include pharmaceutically acceptable carriers as described herein, for example, vehicles, adjuvants, excipients, or diluents, which are well-known to those who are skilled in the art and which are readily available to the public. It is preferred that the pharmaceutically acceptable carrier be one which is chemically inert to the dopamine antagonist and opiate receptor antagonist and one which has no detrimental side effects or toxicity under the conditions of use. The choice of carrier will be determined in part by the particular dopamine antagonist and opiate receptor antagonist, as well as by the particular method used to administer the composition. Accordingly, there is a wide variety of suitable formulations of the pharmaceutical composition employed in accordance with the invention. The following formulations for oral, aerosol, parenteral, subcutaneous, intravenous, intramuscular and interperitoneal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the dopamine antagonist and opiate receptor antagonist, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the dopamine antagonist and opiate receptor antagonist in a flavor, usually sucrose and acacia or tragacanth, as well as pastilles comprising the dopamine antagonist and opiate receptor antagonist in an inert base, such as gelatin and glycerin, or sucrose and acacia, emulsions, gels, and the like containing, in addition to the dopamine antagonist and opiate receptor antagonist, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The dopamine antagonist and the opiate receptor antagonist can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-.beta.-aminopriopionates, and 2-alkyl-imidazoline quaternary ammonium salts, and (3) mixtures thereof.

The invention also provides kits and commercial packages comprising a dopamine antagonist and an opiate receptor antagonist and instructions for use.

The present invention provides pharmaceutical compositions and methods that combine compounds for the treatment or prevention of dependence on a controlled substance, or the treatment or prevention of addictive disorders or diseases, or the treatment or prevention of neurological disorders or diseases.

In one embodiment, the present invention provides methods for treating or preventing dependence on a controlled substance, treating or preventing an addictive disorder or disease, or treating or preventing an neurological disorder or disease an therapeutically effective amount of at least two compounds, and analogs, homologs, derivatives, modifications, and pharmaceutically acceptable salts thereof, selected from the group consisting of dopamine release inhibitors, dopamine antagonists, adrenergic receptor agonists, adrenergic receptor antagonists, 5-HTIA agonists, 5-HTIA antagonists, opioid antagonists, and low dose opioid antagonists.

In one embodiment, the present invention provides compositions and methods for treating or preventing dependence on controlled substances, or addictive disorders or diseases, or neurological diseases or disorders, using pharmaceutical compositions comprising therapeutically effective amounts of levo-tetrahydropalmatine (l-THP) and low dose naltrexone (LDN).

In one embodiment, the present invention encompasses formulating the combination of l-THP and LDN, as well as other drugs, to optimize the invention. In one aspect the drug is formulated as l-THP:LDN. In another aspect the drug is formulated as l-THP:LDN at a ratio of 10:1 to 50:1 or greater. In any embodiment of the present invention, l-THP may be administered in dose of from about 0.5 mg/kg/dose to about 2.5 mg/kg/dose and naltrexone is from about 0.01 mg/kg/dose to about 0.1 mg/kg/dose.

In one embodiment, the present invention encompasses formulating the combination of l-THP and LDN, as well as other drugs, with time-release components to optimize the invention. In one embodiment, the present invention treats or prevents dependence on a controlled substance, addictive disorder or disease, neurological disease or disorder comprising administering to the subject in need thereof, a therapeutically effective combination of l-THP and LDN.

In one embodiment, the dependence on a controlled substance, addictive disorder or disease being treated or prevented includes, but is not limited to addiction, cocaine, methamphetamine, other stimulants, phencyclidine, other hallucinogens, marijuana, sedatives, tranquilizers, hypnotics, nicotine, alcohol and opiates.

In one embodiment, a composition comprising at least two compounds of the invention may be administered at the same time or separately. In one aspect the composition comprises a therapeutically effective dosage of at least two compounds, administered at the same time and using a specific method for delivery to a subject in need thereof that may have a synergistic drug effect. In another aspect, the composition comprises a therapeutically effective combination of both 1-THP and LDN administered at the same time using a specific method for delivery to a subject in need thereof that may have a synergistic drug effect. In one aspect the composition comprises a therapeutically effective dosage of at least two compounds, administered separately and using a specific method for delivery to a subject in need thereof that may have a synergistic drug effect. In another aspect, the composition comprises a therapeutically effective combination of both 1-THP and LDN administered separately using a specific method for delivery to a subject in need thereof that may have a synergistic drug effect.

In one embodiment, a composition comprising at least two compounds of the invention may be administered with another compound of the invention at the same time.

In yet another embodiment, the present invention is directed to method of treating or preventing an addictive behavior in a subject, said method comprising administering to said subject an effective amount of a dopamine antagonist and an opiate receptor antagonist or a composition comprising same wherein said composition is formulated at a ratio of dopamine antagonist to opiate receptor antagonist of about 10:1 to about 50:1. In one aspect of this embodiment, the dopamine antagonist is levo-tetrahydropalmatine provided in an amount of from about 0.5 mg/kg/dose to about 2.5 mg/kg/dose. In one aspect of this embodiment, the opiate receptor antagonist is naltrexone in an amount of from about 0.01 mg/kg/dose to about 0.1 mg/kg/dose.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Effects of Treatment on Cocaine Induced Reinstatement of CPP

Fixed dose l-THP/LDN (3 mg/kg/0.1 mg/kg) were tested in mouse model of CPP. Treatment started after the animal had established a CPP and ended when the animal displayed extinction. While the groups received saline and 0.1 mg/kg naltrexone did not have significant effect on the reinstatement, the groups received 3 mg/kg l-THP or 3 mg/kg l-THP and 0.1 mg/kg naltrexone displayed a significant attenuation on cocaine reinstatement. The combination group exhibited a greater reduction in reinstatement than l-THP alone (FIG. 1).

Example 2

Treatment Effect on Locomotor Activity

Figure 2:
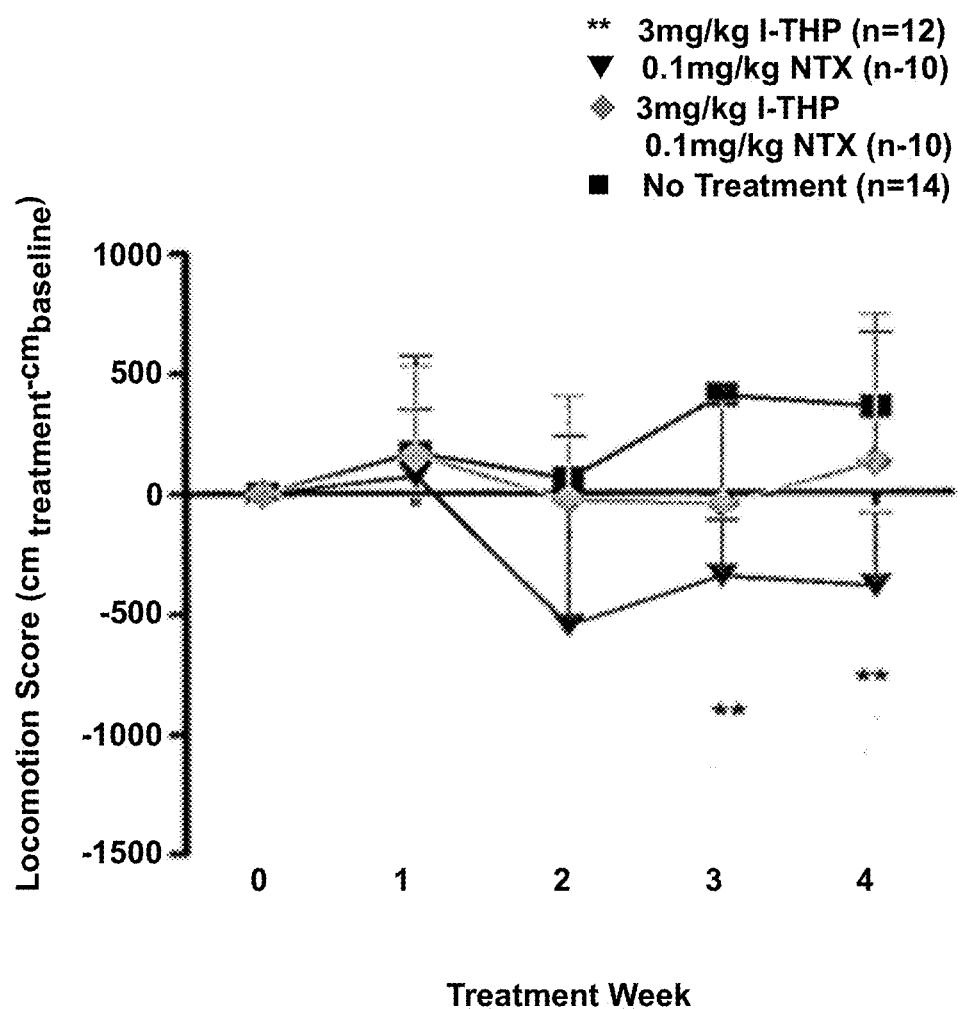
FIG. 2 shows the treatment effect on locomotor activity. Over the course of extinction/treatment the animal's locomotor activity was recorded. The locomotion scores graphed represent the treatment locomotion with the baseline locomotion score subtracted. A two way ANOVA followed by Bonferroni posttest comparison determined that 3 mg/kg l-THP treatment had a significant effect on locomotion during week 3 and week 4 of treatment (**$p<0.01$). 3 mg/kg l-THP combined with 0.1 mg/kg naltrexone had no significant effect on locomotion over the treatment period.

FIG. 2 shows that the 3 mg/kg l-THP treatment reduced locomotor activity significantly during the treatment. l-THP co-administered with LDN reversed the significant decrease in locomotion from the l-THP; and 0.1 mg of Naltrexone alone did not display significant effect on locomotion, indicating a possible synergy occurred at the combination that results in the reverse of l-THP induced locomotor inhibition.

Example 3

Naltrexone Induced Withdrawal

Figure 3:
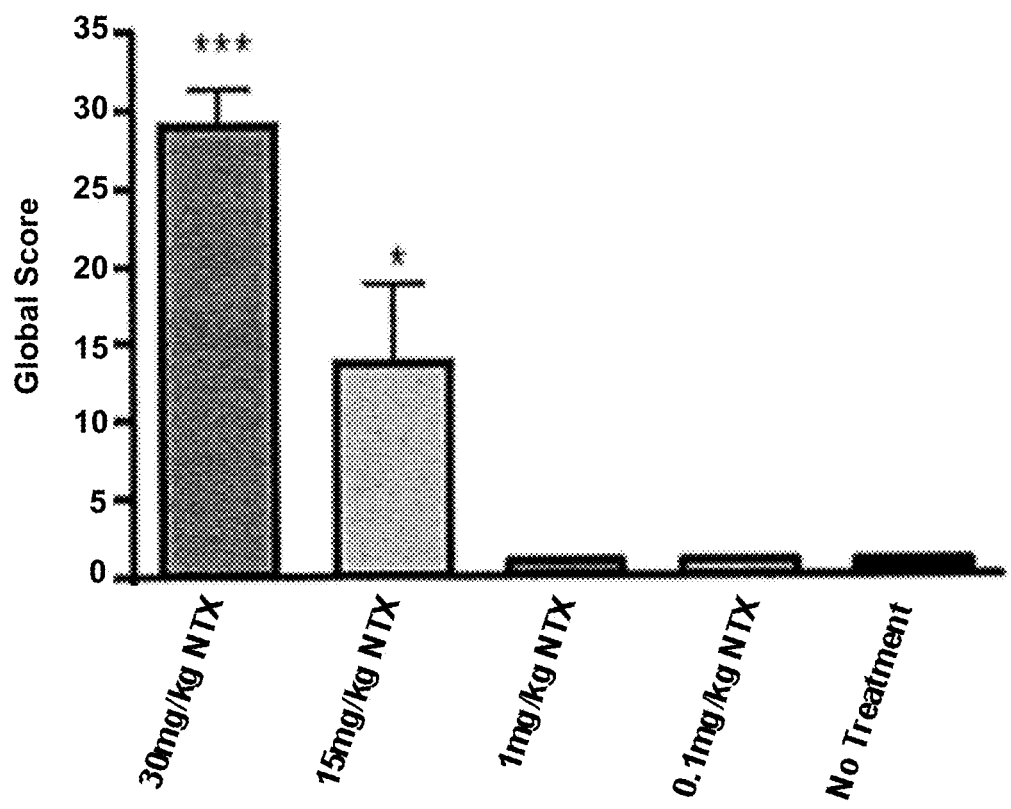
FIG. 3 shows naltrexone induced withdrawal. Animals were treated with 10 mg/kg cocaine over 4 days. On the 5th day animals were injected with different dose of Naltrexone and 3 mg/kg l-THP. After injection animals were monitored for withdrawal behaviors for 20 minutes. Total counts for jumping, teeth chattering, paw tremors and grooming with assigned points were used to calculate the global withdrawal score. A one way ANVOA followed by Bonferroni post test comparisons was used to determine the effect naltrexone dose on withdrawal (***$p<0.001$ and *$p<0.05$ respectively) n=5 for each group. Global Scores were calculated.

When high dose of naltrexone (30 mg/kg, or 15 mg/kg) was co-administered with l-THP in cocaine addicted mice withdrawal symptoms occurred (FIG. 3). This effect was attributed to cocaine's up regulation of endogenous opioids and the significant blockade of opioid receptor by naltrexone. However, lower doses of naltrexone (1 mg/kg, 0.3 mg/kg and 0.1 mg/kg), co-administered with l-THP did not produce withdrawal, indicating it is safe to use LDN in cocaine addicted animals.

Example 4

Safety of l-THP

Data on safety of l-THP in six subjects of cocaine users was generated (Table 1). The major PD/PK parameters of the drug-drug interaction between l-THP and cocaine in cocaine users were compared between active drug and placebo groups. The data indicates that l-THP is safe and well tolerated in cocaine users. The peak changes in heart rate (HR) and blood pressure (BP) were all within acceptable margin. In addition, l-THP pretreatment does not increase the Cmax or AUC0-inf of cocaine (Table 1) indicating its safety for treatment of cocaine addiction. Since l-THP will be 10 fold more than LDN in the combination, the safety of l-THP is the major safety concern in the combination for human drug addicts.

TABLE 1

PD and PK values in Cocaine User Subject Received I-THP and Cocaine

|  | Post cocaine 0 min | | Post cocaine 0 min | |
| --- | --- | --- | --- | --- |
|  | Placebo (n = 3) | I-THP (n = 3) | Placebo (n = 3) | I-THP (n = 3) |
| BP (Change from baseline %) | 10 ± 14/6 ± 2 | 8 ± 9.3/10 ± 13 | 5 ± 2/2 ± 4 | 5 ± 3/5 ± 2 |
| HR (Change from baseline %) | 19.5 ± 30 | 23.6 ± 27.1 | 6.5 ± 1.9 | 8.5 ± 8.1 |

|  |  | Cocaine | | |
| --- | --- | --- | --- | --- |
|  | Unit | Placebo pretreated[a] (n = 3) | I-THP pretreated[b] (n = 2) | I-THP n = 2[b] |
| Cmax | (ng/mL) | 92 ± 46.17 | 88.66 | 38.03 |
| AUC 0-inf | hr * ng/mL | 252.61 ± 102.34 | 296.32 | 392.54 |

[a] mean ± SD,
[b] mean only

The present invention is well adapted to attain the ends and advantages mentioned as well as those that are inherent therein. The embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A pharmaceutical composition consisting of, as active, synergistic substances:
   levo-tetrahydropalmatine; and
   naltrexone in an amount of about 0.01 mg/kg/dose to about 0.1 mg/kg/dose.

2. The composition of claim 1, wherein said composition is formulated as levo-tetrahydropalmatine:naltrexone at a ratio of 10:1 to 50:1.

* * * * *